United States Patent [19]

Hiltebrandt

[11] 4,005,714
[45] Feb. 1, 1977

[54] BIPOLAR COAGULATION FORCEPS

[75] Inventor: Siegfried Hiltebrandt, Knittlingen, Germany

[73] Assignee: Richard Wolf GmbH, Knittlingen, Germany

[22] Filed: July 30, 1975

[21] Appl. No.: 600,462

[30] Foreign Application Priority Data

May 3, 1975 Germany .................... 2519827

[52] U.S. Cl. ............................ 128/303.17; 128/321
[51] Int. Cl.² ..................... A61N 3/04; A61B 17/28
[58] Field of Search ................. 128/303.17, 321

[56] References Cited
UNITED STATES PATENTS

| 463,785 | 11/1891 | Connable et al. ............ 128/321 X |
| 1,472,380 | 10/1923 | Atwood ........................ 128/321 UX |
| 2,002,594 | 5/1935 | Wappler et al. ............... 128/321 X |
| 2,137,710 | 11/1938 | Anderson ........................ 128/321 |
| 3,831,607 | 8/1974 | Lindemann .................. 128/303.17 |
| 3,911,241 | 10/1975 | Jarrard ..................... 128/303.17 X |
| 3,920,021 | 11/1975 | Hiltebrandt ................. 128/303.17 |
| 3,934,589 | 1/1976 | Zimmer ......................... 128/321 X |

Primary Examiner—Channing L. Pace
Attorney, Agent, or Firm—Kinzer, Plyer, Dorn & McEachran

[57] ABSTRACT

Bipolar coagulation forceps in which the forceps coagulate both the fallopian tube and the adjacent mesoslpinx.

8 Claims, 4 Drawing Figures

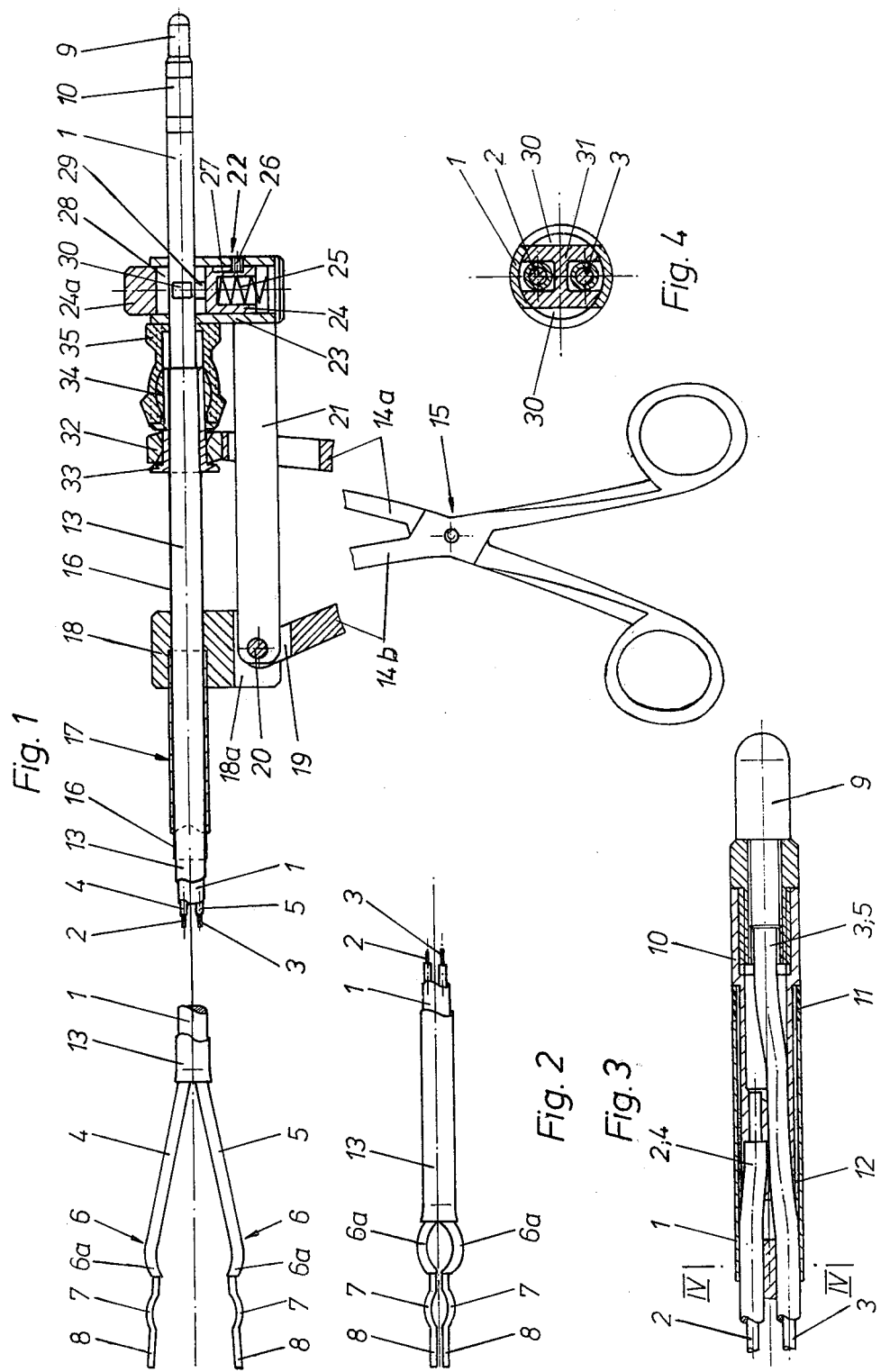

BIPOLAR COAGULATION FORCEPS

The invention relates to a bipolar coagulation forceps of the high frequency type for the coagulation of the Fallopial tubes.

The forceps embodies two insulated current conductors respectively terminating in a coaxial plug and a coaxial contact bushing. The conductors may be resiliently opened and closed by relative longitudinal shifting of an actuating sleeve accomplished with the aid of a handle, in relation to the forceps arms.

In comparison with known prior art devices which generally relate to monopolor high frequency coagulation forceps, where the patient's body is in contact with a grounded plate, the forceps of the present invention avoids uncontrollable dangerous high frequency current transfer in that one salpinx (Fallopian tube) and the neighboring or adjacent mesosalpinx can be seized (clamped) simultaneously and coagulated precisely by the coagulation forceps without causing damage to blood vessels during subsequent severance of the coagulated Fallopian tube in the area of the adjacent mesosalpinx.

According to the invention, a problem is solved in that the portions of the forceps arms distally of the operative high frequency conductors, are insulated parts each having a large curvature (large diameter) used for effectively closing the forceps jaws by means of an actuating sleeve, followed by insulation-free curvatures of less diameter for clamping the Fallopian tube flatly, and then changing into straight, insulation-free flat free ends which during the closing of the forceps will be placed approximately parallel and in contact with opposite sides of the adjacent mesosalpinx. Thus, the forceps jaws embody flat, opposed free end portions for clamping the mesosalpinx and proximate thereto curved portions for embracing and clamping the adjacent Fallopian tube.

Due to this solution, as a result of the strong or large diameter insulated curvatures of the forceps arms, a perfect, flat compression of the salpinx is accomplished by the insulation-free forceps arm parts having the lesser or smaller diameter bend, while simultaneously adjacent to the salpinx the mesosalpinx connected with it is seized or clamped bilaterally by the straight forceps arm parts. Thus, as the high frequency current is turned on a perfect simultaneous coagulation is accomplished of both the salpinx and the mesosalpinx so that subsequently thereto and without danger of bleeding the salpinx can be severed all the way through.

As a result, the salpinx is seized firmly and perfectly and can be pulled freely in the abdominal cavity without sliding out of or escaping from the forceps jaws.

The insulated high frequency conductors are contained within a tubular housing or bushing tube from which the forceps arms protrude and which is firmly connected to an outer support shaft to which one leg of a shear handle is articulated. An actuating sleeve is located between the bushing tube and the support shaft; the other shear handle leg is connected to this sleeve so that the distal end of the sleeve can be urged against the proximal side of the large diameter insulated curvature of the forceps arms to produce quick and firm clamping of the body tissue being treated.

The forceps once closed will remain closed with the shear handle closed, and the salpinx with the mesosalpinx can be manipulated freely in the abdominal cavity, so that subsequently, and without danger to other organs, coagulation is performed.

As will be explained further in detail, the coagulation forceps are so designed that its individual parts can be separated from each other easily and conveniently, so that they can be sterilized perfectly, and then reassembled.

In the drawing:

FIG. 1 shows a discontinuous lateral view of the bipolar coagulation forceps according to the invention partly sectioned, with opened forceps jaws;

FIG. 2 shows the distal end of the coagulation forceps with the forceps jaws closed;

FIG. 3 shows a longitudinal section through the proximal end of the enveloped current conductors; and FIG. 4 shows a cross-section along line IV—IV of FIG. 3.

According to the embodiment shown in the drawing, the bipolar high frequency coagulation forceps comprises a tubular housing or bushing tube 1 through which two high frequency conductors 2, 3 extend which are each surrounded by insulation 4 and 5. These conductors are normally spread divergently and resiliently at the distal end to afford spring-like forceps arms 6. The conductors with the insulation 4, 5 protrude from tube 1 and are configured to define outwardly convex curvatures 6a. Forward of the curvature 6a, the conductors are free from insulation and are configured to afford outwardly convex curvatures 7 of less diameter than the curvatures 6a. The conductors terminate in straight tip portions 8 which define the free ends of the jaws. Advantageously, at least the forceps arm parts 7 and 8 have flat opposed surfaces of generous width to accomplish wide coagulations at the salpinx and mesosalpinx.

The one conductor 3 ends in a coaxial plug 9 and the other conductor terminates in a plug bushing 10 insulated against the plug 9 and having a larger diameter. The plug bushing 10 is insulated at 11, and additionally, by an insulating tube 12, against the enveloping tube 1.

Tube 1 is surrounded by an actuating sleeve 13 which is connected to the one leg 14a of a shear handle 15 in a manner now to be described. The connection of the actuating shaft or sleeve 13, which is slightly flared at the distal end, with the shear handle leg 14 is accomplished in that an apertured end 32 of the leg 14a is pressed on to a bushing 33, secured to shaft 13, provided with a collar and held in place by a retainer 34 threadedly mounted on the bushing 33. A rubber cap 35 affording a seal between the actuating sleeve 13 and the housing 1 is placed over the retainer 34. For better guidance in an outer support shaft 17, sleeve 13 may be surrounded over a portion of its length by a reinforcing tube 16. The outer shaft 17 terminates in a bearing jack 18.

The fork end 19 of the second shear handle leg 14b is mounted on a cross pin 20 in a lower recess 18a of the bearing jack and a longitudinally extending strut 21 is articulated to the fork 19 by the pin 20. Strut 21 freely passes through shear leg 14a and is rigidly connected by a coupling 22 to the bushing tube 1. As a result of this design the outer shaft 17 is rigidly connected to the bushing tube 1.

The coupling 22 comprises a cylindrical housing 23 fastened to the strut 21. A slide 24 is shiftably mounted in the housing 23, while being externally actuatable and spring-biased by a pressure spring 25. Movement of slide 24 is limited by a set screw 26 which engages an axis-parallel groove 27 in the slide. The housing 23 is cross-drilled for the passage of the bushing tube 1. The slide protrudes from housing 23 to present a push button 24a having an opening 28 for the bushing tube 1 passing through, commensurate with the limited displaceability of the slide.

To establish the coupling, the slide 24 is provided in the longitudinal passage 28 with two oppositely placed lands or protrusions 29 which engage into lateral recesses 30 of the bushing tube 1, thereby establishing the coupling. To compensate for weakening of the bushing tube 1 due to the lateral recesses 30, a reinforcing profile part 31 is inserted into the bushing tube 1 (FIG. 4).

By actuating the shear handle 15 into closing position the shaft 13 is advanced relative to the tubular members 1 and 17, and at first urges, with its flared distal end, the insulated forceps arm parts 6 towards each other and then cams against the strong curvatures 6a, so that the forceps jaws formed by the curvatures 7 are closed, whereby the straight parts 8 engage each other, as shown in FIG. 2. Once the coagulation forceps has thus been introduced into the abdominal cavity through a trocar guide (not shown), the forceps is reopened by retracting sleeve 13, due to the spring return effect of the divergent forceps arms. Now the forceps jaws are so directed under observation of the surgeon that the salpinx or Fallopian tube to be coagulated lies within the small curvatures 7 whilst the straight forceps arm parts 8 lie in the range of the adjacent mesosalpinx, whereupon the forceps is closed by actuation of the shear handle 15; the walls of the salpinx (Fallopian tube) are compressed flatly or squeezed by the lesser curvatures 7 and the straight arm parts 8 clamp opposite sides of the adjacent mesosalpinx. Now the salpinx is manipulated with the mesosalpinx in the abdominal cavity, without disengaging the forceps which remain closed, and then the high frequency current is turned on. At first the mesosalpinx is coagulated and eventually the blood vessels in the proximity of the salpinx, due to the slight distance of the straight arm parts 8, and then the flattened salpinx coagulates. After a certain cooling period the forceps is opened and then the salpix can be severed and/or cut through, without any bleeding occuring due to vascular damages adjacent to the salpinx in the area of the mesosalpinx.

Following the use, the individual parts of the bipolar coagulation forceps according to the invention can easily be disassembled for sterilization. For this purpose the slide 24 of the coupling is depressed against the spring means 25 by actuating the button 24a, whereby parts 29 and 30 are disengaged, so that tube 1 can be extracted along with the conductors 2, 3. Then the coupling 22 hangs down loosely at the strut 21. The rubber cap 35 is then pulled off and the retainer 34 is removed, enabling the grip ring 32 to be slid off bushing 33. Shaft 13 may then be extracted. Finally the pin 20 can be removed, so that the outer shaft 17, the entire shear handle 15 and the coupling 22 with the connecting strut 21 likewise are free individual parts.

I claim:

1. Bipolar frequency coagulation forceps for the coagulation of the Fallopian tubes, said forceps including two insulated current conductors affording a pair of resiliently spreading forceps arms which are closed by relative longitudinal shifting of an actuating sleeve accomplished with the aid of a handle, portions of the forceps arms located proximally to free ends of the conductors being insulated and each having a first curvature for closing the forceps by means of said sleeve, and having insulation-free second curvatures of less diameter than said first curvature located between said first curvature and said free end for clamping a Fallopian tube, and the free ends of the conductors being straight and insulation-free, adapted during the closing of the forceps to be placed approximately parallel to one another on opposite sides of the adjacent mesosalpinx.

2. The coagulation forceps according to claim 1, characterized by the fact that at least the opposed surfaces of the insulation-free parts are flat.

3. The coagulation forceps according to claim 2, further characterized by the conductors being contained within a tubular housing from which the forceps arms protrude, said housing being connected to an outer support shaft which supports one leg of a shear handle, and an actuating sleeve positioned concentrically between the housing and the support shaft, said actuating sleeve being connected to the other shear handle leg and having a distal end engageable with the proximal side of the insulated second curvature of the forceps arms.

4. The coagulation forceps according to claim 3, further characterized in that said one shear handle leg is connected by a strut to a coupling removably attached to the housing.

5. The coagulation forceps according to claim 4, further characterized in that the actuating sleeve is removably connected to the other shear handle leg and that a seal is provided between the actuating sleeve and the housing.

6. The coagulation forceps according to claim 4, further characterized in that the coupling part consists of a cylindrical housing provided with a transverse opening for receiving the housing and in which a spring-biased slide is located, said slide having a protuberance engaged with a recess in the housing, and said slide being manually depressable to disengage said protuberance.

7. The coagulation forceps according to claim 5, further characterized in that a bushing is located at the proximal end of the actuating sleeve for supporting an apertured end of the one shear handle leg and that a retainer is screwed to the threaded end of the bushing.

8. The coagulation forceps according to claim 7, further characterized in that the actuating sleeve is flared at the distal end.

* * * * *